United States Patent [19]

Matsuda

[11] 4,118,124
[45] Oct. 3, 1978

[54] HOLOGRAPHIC SHEARING INTERFEROMETER

[75] Inventor: Kiyofumi Matsuda, Musashi-Murayama, Japan

[73] Assignee: Agency of Industrial Science & Technology, Tokyo, Japan

[21] Appl. No.: 744,235

[22] Filed: Nov. 23, 1976

[30] Foreign Application Priority Data

Nov. 26, 1975 [JP] Japan .................... 50-141506

[51] Int. Cl.$^2$ .............................................. G01B 9/02
[52] U.S. Cl. ...................... 356/107; 356/111; 350/3.73
[58] Field of Search ............... 356/109, 107, 111; 350/3.5, 3.70, 3.73

[56] References Cited

U.S. PATENT DOCUMENTS

| | | | |
|---|---|---|---|
| 3,468,609 | 9/1969 | Sterrett | 356/107 |
| 3,532,431 | 10/1970 | Bryngdahl | 350/3.5 |
| 3,572,934 | 3/1971 | Bryngdahl | 350/3.5 |
| 3,923,400 | 12/1975 | Hardy | 356/111 |

*Primary Examiner*—Conrad J. Clark
*Attorney, Agent, or Firm*—Kurt Kelman

[57] ABSTRACT

The sheared interference fringe of a wavefront from an object under test is obtained by recording on a first hologram the interference fringe formed between a first reference light beam and two light beams having slightly different angles of incidence with respect to the first hologram, recording on a second hologram the interference fringe formed between a second reference light beam and the two light beams reconstructed by an illuminating light beam incident on the first hologram from the same direction as the first reference light beam, placing the first and second holograms thus obtained at a prescribed distance from each other, causing a light beam from the object under test to impinge upon the first hologram from the same direction as the first reference light beam to produce light beams and projecting the produced light beams upon the second hologram for thereby causing the second hologram to produce light beams in the same direction as the second reference light beam.

8 Claims, 14 Drawing Figures

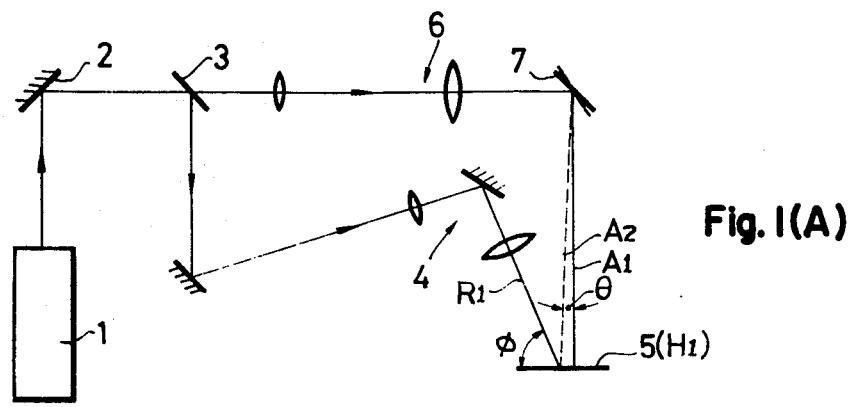
Fig. I(A)
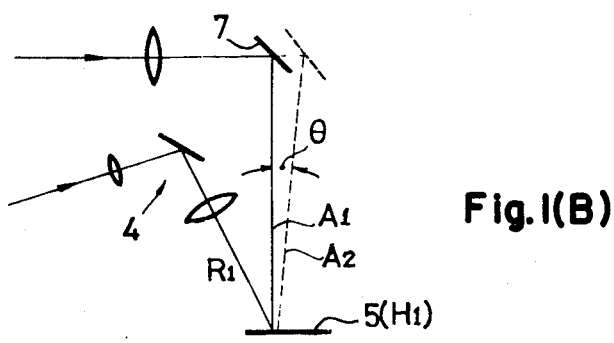
Fig. I(B)
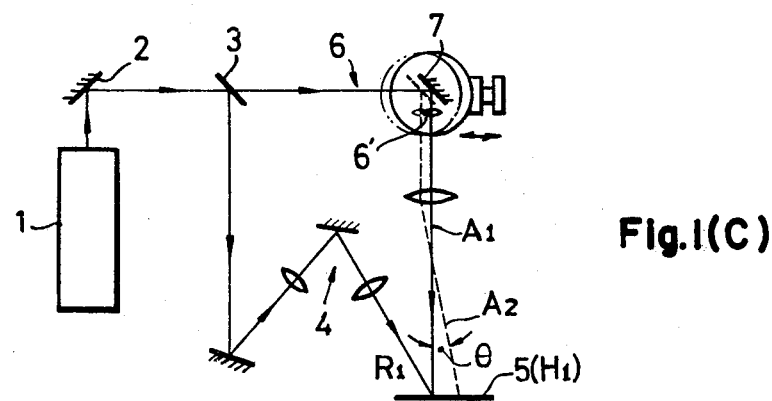
Fig. I(C)

HOLOGRAPHIC SHEARING INTERFEROMETER

BACKGROUND OF THE INVENTION

This invention relates to a method for shearing a wavefront of an object under test by using two holograms as the interferometer and to a shearing interferometer to be used for effecting said method.

Heretofore, such devices as the Ronchi-grating and the Mach-Zehnder interferometer have generally been adopted for the determination of lens aberration, distribution of refractive index in glass plates, distribution of refractive index in fluids, and so on. With the Ronchi-grating, since the maximum available area for producing the interference patterns is 50%, the field of vision is narrow, the contrast of produced interference fringe is not sharp and the degree of shearing cannot be varied. The Mach-Zehnder interferometer is deficient in optical stability and is complicated in adjustment because it is not a common path type instrument.

The hologram has to date been employed generally as a medium for recording. In the conventional shearing interferometry using the hologram, therefore, it has been necessary to use a complicated optical system because the interference fringe of a wavefront from an object under test has been recorded on an individual basis on each hologram. By this method of shearing interferometry, it is difficult to carry out the desired measurement easily at a desired place. Further, since this method inevitably requires the photographic plate containing the recorded image to be developed, it does not permit real-time observation of shearing interferometry.

An object of this invention is to provide a shearing interference which provides the desired amount of shear of the interference fringe of an object with extreme ease at any desired place.

Another object of the present invention is to provide a shearing interferometer which permits ready variation of the amount of shear and which enables the shearing of the interference fringe to be obtained with high accuracy.

SUMMARY OF THE INVENTION

To attain the objects described above according to the present invention, there is provided a method for shearing interferometry, which comprises producing a first hologram using an interference fringes formed between one first parallel reference light beam and either two parallel light beams or two divergent light beams having slightly different angles of incidence, producing a second hologram using an interference fringe formed between one second parallel reference light beam and the light beams reconstructed by a parallel illuminating light beam incident on the first hologram from the same direction as the first reference light, disposing the first and second holograms thus produced at a prescribed distance from each other so that the two holograms as a set serve as a holographic interferometer, causing a light beam from the object under test to impinge on the first hologram from the same direction as the first reference light beam for thereby causing the first hologram to produce light beams projecting the produced light beams upon the second hologram for thereby causing the second hologram to produce light beams in the same direction as the second reference light beam, causing the last produced light beams to produce an image of the object under test and, through visual observation of the image, determining the sheared interference fringe representing the differential value of the wavefront produced by the object.

Since in the method of this invention, the operation involved simply comprises preparing in advance two holograms on which the specific interference fringe has already been recorded and, at the time of observation of the phenomenon, disposing the two holograms at a prescribed distance from each other, desired shearing interferometry can easily be carried out at a desired place. The amount of shear in this case can be changed by varying the distance by which said two holograms are separated from each other. Thus, shearing interferometry can be carried out with accuracy on various objects by suitably adjusting the amount of shear in accordance with variations in the refractive indices of the objects under test.

The other objects and other characteristics of the present invention will become apparent from the description to be given in detail hereinbelow with reference to the accompanying drawing.

BRIEF DESCRIPTION OF THE DRAWINGS

FIGS. 1(A), 1(B) and 1(C) are explanatory views illustrating the preparation of the first hologram in the holographic shearing interferometer of the present invention.

DESCRIPTION OF THE PREFERRED EMBODIMENTS

Figure 2A:
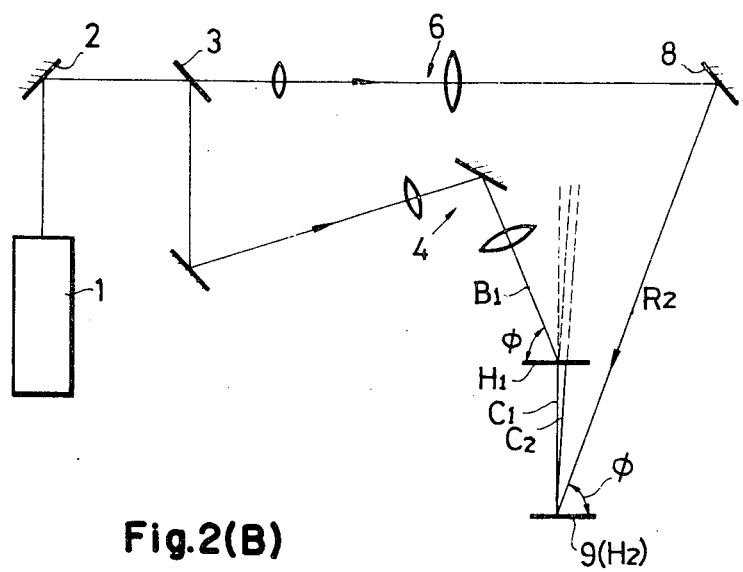
FIGS. 2(A) and 2(B) are explanatory views illustrating the preparation of the second hologram in the holographic shearing interferometer of this invention.

In the method of this invention for the shearing interferometry, two holograms are used as the shearing interferomter. A description will, therefore, first be made on the preparation of these two holograms. Referring to FIG. 1(A), the first hologram $H_1$ is prepared by dividing the laser beam from, for example, a He-Ne gas laser 1 into two beams by means of a beam splitter 3 aided by a reflecting mirror 2, collimating one of the beams and projecting it as the parallel reference light $R_1$ onto a photographic plate 5 by means of an optical system 4 and, at the same time, collimating the other beam by an optical system 6 and then projecting it onto the photographic plate 5 via a reflecting mirror 7, with the inclination of said reflecting mirror 7 being slightly varied so as to produce two collimated light beams $A_1$ and $A_2$ having slightly different angles of incidence, for thereby through double exposures recording on said photographic plate 5 the interference fringe formed between the reference light beam $R_1$ and said two collimated light beams $A_1$ and $A_2$ and subjecting the photographic plate 5 to photographic processing.

The foregoing embodiment has been described as involving simultaneous recording of the interference fringe between the collimated light beams $A_1$ and $A_2$ and the reference light beam $R_1$. Alternatively, the interference fringe formed between the collimated light beam $A_1$ and the reference light beam $R_1$ may be recorded first on the photographic plate 5 and subsequently the interference fringe formed between the collimated light beam $A_2$ and the same reference light beam $R_1$ recorded on one and the same photographic plate 5. Formation of said two collimated light beams $A_1$ and $A_2$ may be accomplished by slightly shifting the position of the reflecting mirror 7 and rotating the mirror by a prescribed angle as illustrated in FIG. 1(B). They may otherwise be obtained by simply causing a movable base carrying thereon the reflecting mirror 7 and a lens 6' to be translated along the axis of light as illustrated in FIG. 1(C).

The second hologram $H_2$ is prepared, as illustrated in FIG. 2(A), by projecting a laser light beam $B_1$ onto the first hologram $H_1$ prepared as described above in the same direction as that of said reference light beam $R_1$ for thereby causing the illuminating light beam $B_1$ to produce light beams $C_1$ and $C_2$ corresponding to the two collimated light beams $A_1$ and $A_2$ having slightly different angles of incidence, recording on a photographic plate 9 the interference fringe formed between the reference light beam $R_2$ projected via a reflecting mirror 8 and said produced light beams $C_1$ and $C_2$ and thereafter subjecting the photographic plate 9 to photographic processing.

The foregoing preparation of the second hologram $H_2$ has been described as making use of the light beams reconstructed by the first hologram $H_1$. It may otherwise be prepared independently as illustrated in FIG. 2(B).

Figure 2B:
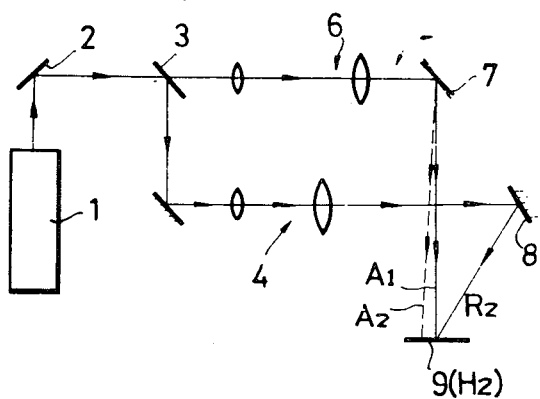

Referring now to FIG. 2(B), the second hologram $H_2$ can be prepared by dividing the laser beam from a laser 1 into two beams by passing the laser beam via a reflecting mirror 2 and a beam splitter 3, collimating one of the two resulting beams by an optical system 4, projecting the collimated light beam as the reference light beam $R_2$ onto a photographic plate 9 via a reflecting mirror 8 and, at the same time, collimating the other laser beam and projecting the collimated light beam onto the same photographic plate 9 via a reflecting mirror 7, with the inclination of the reflecting mirror 7 being slightly varied so as to produce two collimated light beams $A_1$ and $A_2$ having slightly different angles of incidence in entirely the same way as the two collimated light beams are used in the preparation of the first hologram $H_1$, for thereby recording on said photographic plate 9 through double exposure the interference fringe formed between the reference light beam $R_2$ and said two collimated light beams $A_1$ and $A_2$ and subjecting the resultant photographic plate 9 to photographic processing. In this case, the distance separating the reflecting mirror 7 and the photographic plate 9 must be greater than in the preparation of the first hologram $H_1$.

Preparation of the second hologram $H_2$ may otherwise be accomplished by producing two first holograms $H_1$ and using an extra hologram as the second hologram.

The angle $\theta$ which is formed by the two parallel light beams $A_1$ and $A_2$ must satisfy the requirement that the two light beams $C_1$ and $C_2$ produced by the first hologram $H_1$ should effectively irradiate the second hologram $H_2$. This requirement is fulfilled when the value of $\theta$ satisfies the expression $\tan \theta < a/D$. In this expression, "$a$" denotes the diameter of the smallest of the light beams among the collimated light beams $A_1$ and $A_2$ and the two reference light beams $R_1$ and $R_2$ which are utilized in the preparation of the first and second holograms and "$D$" denotes the distance which separates the first hologram $H_1$ and the second hologram $H_2$ at the time of the measurement.

Where there exists the relationship of $\tan \theta \geq a/D$, the two produced light beams $C_1$ and $C_2$ do not converge into each other and, therefore, fail to produce an interference fringe (FIG. 2).

Figure 3:
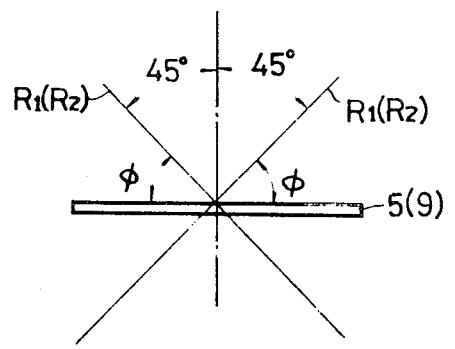
FIG. 3 is an explanatory view illustrating the angle of projection of the reference light beam as involved in FIG. 1 or 2.

As regards the angle at which the reference light beams $R_1$ and $R_2$ impinge upon the photographic plates 5 and 9, if this angle is so small that the interval between the interference rings recorded on the holograms becomes smaller than the thickness of the emulsion deposited on the photographic plate, then there ensues a phenomenon of black diffraction and the contrast of the shearing interferograms becomes weak. The practical range of the angles of incidence for the reference light beams $R_1$ and $R_2$ is from 45° to 90° (FIG. 3).

In the present invention, the two holograms $H_1$ and $H_2$ prepared as described above are disposed at a prescribed distance from each other and these two holograms together consequently form a shearing interferometer. A description will now be made of the method by which the wavefront of an object subjected to measurement is determined by use of this shearing interferometer, with reference to FIG. 4.

Figure 4:
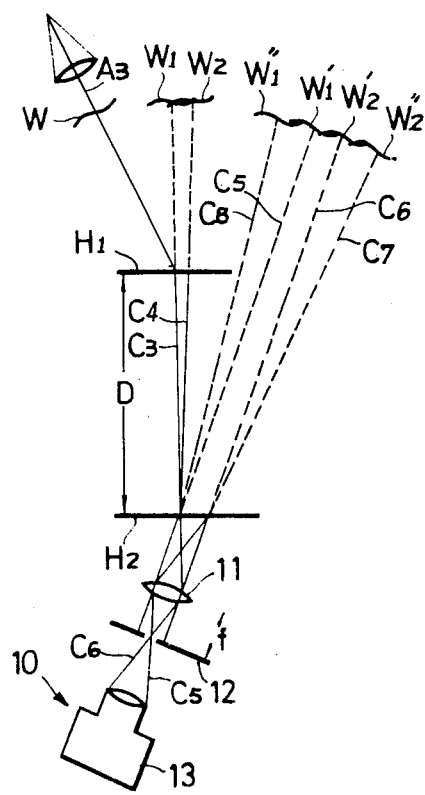
FIG. 4 and FIG. 5 are explanatory views illustrating the measurement of wavefront of the object due to shearing interference by use of the holographic shearing interferometer of this invention.
Figure 5:
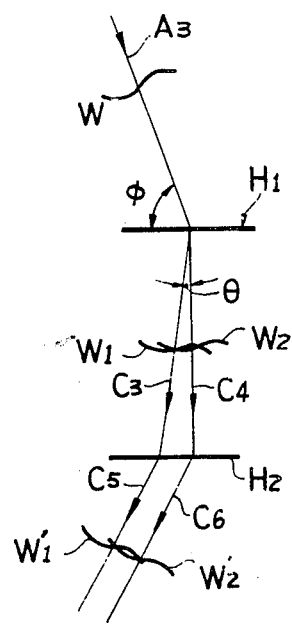

Referring to FIG. 4, the holograms $H_1$ and $H_2$ are positioned at a prescribed distance D from each other and the wavefront W from the object subjected to test is made to impinge on the hologram $H_1$ from a direction corresponding to that of the reference light beam $R_1$. The object is irradiated by the collimated light beam $A_3$ and the hologram $H_1$ is produced by the light emitted from the wavefront W. Consequently, the wavefront W is constructed in the form of virtual images in the direction of the collimated light beams $A_1$ and $A_2$ (FIG. 5). Since the wavefronts $W_1$ and $W_2$ thus constructed are inclined by an angle of $\theta$ each other, they are sheared and at the same time tilted. When the interference fringe formed by the constructed light beams $C_3$ and $C_4$ is visually inspected, it is noted that the effect of said tilting appears to predominate over that of the shearing.

Figure 6:
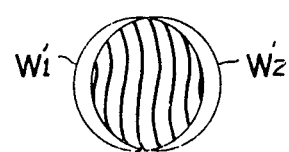
FIG. 6 is an explanatory view illustrating the condition of shearing interference carried out by application of the operation illustrated in FIG. 4 or 5.

The second hologram $H_2$ serves the purpose of eliminating the effect of the tilting. The second hologram $H_2$ is irradiated by the reconstructed light beams $C_3$ and $C_4$ produced by said first hologram $H_1$. Consequently, the light beams $C_5$ and $C_6$ produce wavefronts $W_1'$ and $W_2'$ in the form of virtual images in the direction of the reference light beam $R_2$ for the second hologram $H_2$. These wavefronts $W_1'$ and $W_2'$ are compensated for in inclination and are in accurately sheared form. At the same time, the light beams $C_7$ and $C_8$ reconstruct virtual images $W_1''$ and $W_2''$ in the form of ghost images (FIG. 4). The light beams $C_5$ and $C_6$ which give rise to the wavefronts $W_1'$ and $W_2'$ in the form of virtual images can be selectively separated by intercepting the light beams $C_7$ and $C_8$ by placing a pinhole or stopper 12 at the position of the focal length "$f$" of the lens 11 in the observation means 10. As illustrated in FIG. 6, a shearing interferogram is formed where the light beams $C_5$ and $C_6$ converge to meet each other. Thus, by means of a camera incorporated in the observation means 10 or through visual observation from a point immediately behind the stopper 12, the determination of the wavefront W by the shearing interferometry can be accomplished.

In the shearing interferometry to be carried out by the method described above, the amount of shear may be varied for the purpose of facilitating the observation of the interference fringe. Now, the method of varying the amount of shear will be described with reference to FIG. 7.

The amount of shear $\Delta S$ is roughly equal to the product of the distance D separating the two holograms multiplied by the angle $\theta$ formed by the two collimated light beams, as shown below.

$$\Delta S = D \cdot \theta$$

Figure 7A:
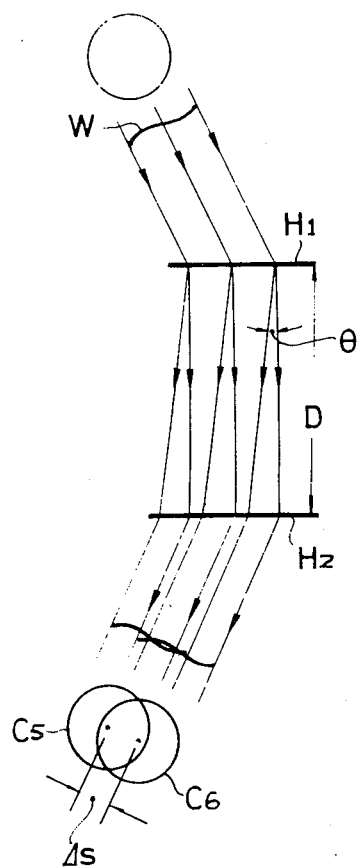
FIGS. 7(A) and 7(B) are explanatory views illustrating the relation between the change in the distance separating the two holograms and the change in the amount of shear as observed in the operation of the holographic shearing interferometer of this invention.
Figure 7B:
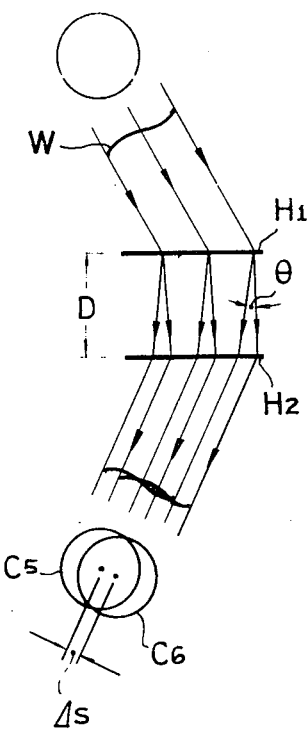

In the preceding equation, the angle $\theta$ is fixed at the time that the holograms are prepared. Thus, the amount of shear $\Delta S$ varies proportionally with the distance D between the pair of holograms $H_1$ and $H_2$. As illustrated in FIG. 7(A), the amount of shear decreases as the distance between the holograms $H_1$ and $H_2$ decreases. The amount of shear $\Delta S$ increases with the increasing distance between the holograms $H_1$ and $H_2$ (FIG. 7(B)).

Figure 8:
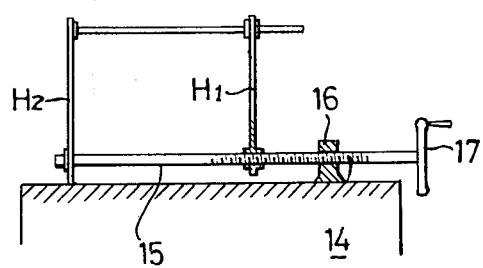
FIG. 8 is a side view illustrating one embodiment of the means for adjusting the distance between the two holograms in the construction of FIG. 7.

One method by which the distance separating the two holograms $H_1$ and $H_2$ can be varied will be described with reference to FIG. 8. The second hologram $H_1$ is fastened on a base 14 and the first hologram $H_2$ is fastened to a rod 15 in a direction parallel with that of the second hologram $H_2$. When the rod 15 is rotated by a handle 17, it is moved forward or backward by means of the nut 16 which is adapted to carry the rod 15 and fastened to the base 14. Thus, the distance separating the two holograms can easily be adjusted.

Any of various other known methods can be adopted for the adjustment of the distance between these two holograms $H_1$ and $H_2$.

The preceding embodiment has been described as causing the shearing interferometry by use of collimated light beams. Said collimated light beams may be replaced with divergent lights.

Figure 9:
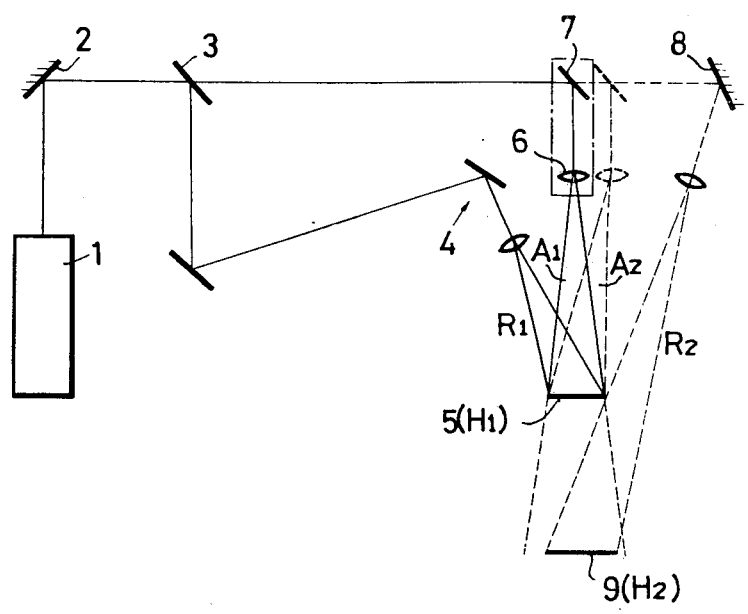
FIG. 9 is an explanatory view illustrating another embodiment of the preparation of the first and second holograms in the holographic shearing interferometer of this invention.

FIG. 9 illustrates a case of shearing interferometry effected by using divergent lights. Fundamentally, this embodiment is identical with the preceding embodiment.

In the embodiment of FIG. 9, the first hologram $H_1$ is prepared by dividing a laser beam from a laser 1 into two beams by means of a beam splitter 3, converting one of the two beams into a divergent light beams by an optical system 4, projecting the divergent light beams as the reference light $R_1$ onto a photographic plate 5 and, at the same time, projecting the other split beam onto the same photographic plate 5 with the aid of a reflecting mirror 7 and an optical system 6, with said reflecting mirror 7 and optical system 6 mounted stationarily such as on a supporting base and moved thereby so as to produce two divergent light beams $A_1$ and $A_2$ having slightly different angles of incidence, and recording on the photographic plate 5 through double exposure the interference fringe formed between the reference light beam $R_1$ and the divergent light beams $A_1$ and $A_2$.

The second hologram $H_2$ is similarly prepared by projecting a divergent light beam as an illuminating light onto the first hologram $H_1$ in the same direction as that of the aforementioned reference light beam $R_1$, recording on a photographic plate 9 the interference fringe formed between the resultant reconstructed light beams and the reference light beam $R_2$ projected by the reflecting mirror 8 and developing the image on the plate 9 by photographic processing.

Desired shearing interferometry by use of the first hologram $H_1$ and the second hologram $H_2$ prepared as described above can be carried out in much the same way as in the first embodiment. To be specific, the measurement is effected by placing the first and second holograms $H_1$ and $H_2$ at a prescribed distance from each other, setting the wavefront W of an object in the direction of the reference light $R_1$ and irradiating said wavefront W with a divergent light.

A relatively large holographic shearing interferometer can be obtained by using divergent lights from such a point source as this, whereas the diameter of the light beam is limited to the size of the lens in use when collimated light beams are used as described above. Furthermore, in using a lens to produce collimated light beams care must be taken to eliminate lens aberration as much as possible, whereas there is no need for such a lens when divergent lights are used.

Figure 10:
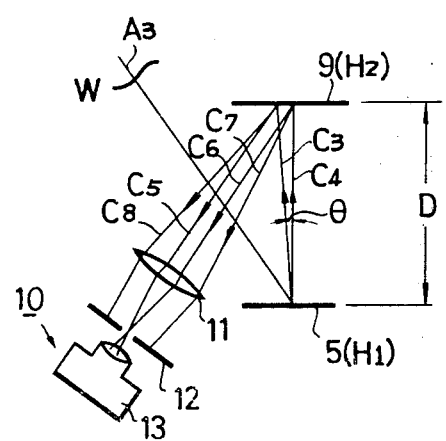
FIG. 10 is an explanatory view illustrating another embodiment of the holographic shearing interferometer according to the present invention.

The preceding embodiments have invariably been described as effecting shearing interferometry by use of a set of penetrable holograms. Reflective photoresists can take the place of photographic plates in the preparation of holograms. Now, by reference to FIG. 10, a description will be made of shearing interferometry effected by using photoresists instead of photographic plates.

The first hologram $H_1$ is prepared by setting up an optical system similar to that of FIG. 1(A), placing a photoresist at the same position as that of a photographic plate, projecting a laser beam from a laser 1 and recording on said photoresist the interference fringe formed between a reference light beam $R_1$ and two parallel light beams $A_1$ and $A_2$.

The second hologram $H_2$ is prepared by setting up an optical system as illustrated in FIG. 2(B). In this case, the second hologram $H_2$ can be obtained without use of any reconstructed light. For the first and second holograms prepared as described above to become reflective holograms, they must have their surfaces coated with aluminum film by means of vacuum deposition.

The pair of reflective holograms $H_1$ and $H_2$ obtained as described above are disposed, as illustrated in FIG. 10, at a prescribed distance D from each other, with their respective reflecting surfaces looking to each other. An object subjected to interferometric measurement is positioned in the direction of the reference light beam $R_1$. Now, a collimated light beam $A_3$ is projected to irradiate the first hologram $H_1$. Then, the hologram $H_1$ is constructed by the light emitted from the wavefront W. Consequently, light beams $C_3$ and $C_4$ produced by the first hologram are reflected to irradiate the second hologram $H_2$. The second hologram $H_2$ constructed wavefronts $W_1'$ and $W_2'$ in the form of virtual images from the light beams $C_5$ and $C_6$ and virtual images $W_1''$ and $W_2''$ in the form of ghost images from light beams $C_7$ and $C_8$, all in the direction of the reference light beam $R_2$. By having the light beams $C_7$ and $C_8$ intercepted with a pinhole or stopper 12, therefore, desired shearing interferometric measurement of the wavefront W can be obtained. The amount of shear can be changed by varying the distance D separating the two photoresists $H_1$ and $H_2$.

In the shearing interferometer using such reflective holograms, possible loss of the quantity of light from the object under test is smaller than in the shearing interferometer using penetrable holograms.

As described in full detail above, the method of the present invention permits the shearing interferometric measurement to be accomplished with extreme ease at any desired place by use of a shearing interferometer composed of two holograms. As is plain from the construction of this apparatus, the aberration of holograms has no adverse effect on the interference fringe and the adjustment of the amount of shear can be effected with extreme simplicity. Thus, the method of this invention can be utilized quite effectively for inspection of lenses and mirrors, for determination of shapes of phase of objects, in differential interference microscopes, and so on.

What is claimed is:

1. A method for the holographic shearing interferometry, which comprises producing a first hologram using an interference fringe formed between a first reference light beam and two light beams having slightly different angles of incidence, producing a second hologram using an interference fringe formed between a second reference light beam and the light beams produced by an illuminating light beam projected on said first hologram from the direction of said first reference light beam, disposing the first hologram and the second hologram at a prescribed distance from each other, causing a light beam from an object to irradiate said first hologram from the direction of said first reference light beam and projecting the light beams produced by said first hologram onto the second hologram for thereby causing the second hologram to reconstruct light beams in the direction of said second reference light beam, whereby the sheared interference fringe of the object is obtained in last reconstructed light beams.

2. The method according to claim 1, wherein the two incident light beams and the one reference light beam are collimated light beams.

3. The method according to claim 1, wherein the two incident light beams and the one reference light beam are divergent light beams.

4. The method according to claim 1, wherein the distance between said first hologram and said second hologram is adjustable.

5. A holographic shearing interferometer, comprising in combination a first hologram produced by an interference fringe formed between a first reference light beam and two light beams having slightly different angles of incidence, a second hologram produced by an interference fringe formed between a second reference light beam and the light beams constructed by an illuminating light beam projected on the first hologram from the direction of said first reference light beam, with said first hologram and said second hologram disposed at a prescribed distance from each other, means for causing a light beam from an object to irradiate the first hologram from the direction of said first reference light beam and means for producing the sheared interference fringe of said object from the light beam reconstructed by said second hologram in the direction of said second reference light.

6. The holographic shearing interferometer according to claim 5, wherein said first hologram and said second hologram are produced on photographic plates.

7. The holographic shearing interferometer according to claim 5, wherein said first hologram and said second hologram are produced on photoresists.

8. The holographic shearing interferometer according to claim 5, further comprising means for adjusting the distance between said first hologram and said second hologram.

* * * * *